United States Patent [19]

Deutsch et al.

[11] 4,207,593

[45] Jun. 10, 1980

[54] METHOD AND APPARATUS FOR THE AUTOMATIC RECOGNITION AND EVALUATION OF OPTICAL CRACK INDICATIONS ON THE SURFACE OF WORKPIECES

[75] Inventors: Volker Deutsch, Wuppertal-Elberfeld; Ernst-August Becker, Sprockhövel-Schee; Ulrich Förstermann, Sprockhövel, all of Fed. Rep. of Germany

[73] Assignee: Karl Deutsch Prüf- und Messgerätebau GmbH & Co. KG, Wuppertal, Fed. Rep. of Germany

[21] Appl. No.: 819,610

[22] Filed: Jul. 27, 1977

[30] Foreign Application Priority Data

Jul. 31, 1976 [DE] Fed. Rep. of Germany ....... 2634505
Aug. 4, 1976 [DE] Fed. Rep. of Germany ....... 2635042

[51] Int. Cl.² .............................................. H04N 7/18
[52] U.S. Cl. .................................... 358/106; 250/562
[58] Field of Search ................ 358/106, 107; 364/507; 250/562, 563, 572; 356/200, 237, 239, 240, 420

[56] References Cited

U.S. PATENT DOCUMENTS

| | | | |
|---|---|---|---|
| 3,295,362 | 1/1967 | Wood et al. | 364/507 |
| 3,480,855 | 11/1969 | Lorenzi | 358/106 |
| 3,647,961 | 3/1972 | Blitchington, Jr. et al. | 358/106 |
| 3,988,530 | 10/1976 | Ikegami et al. | 250/562 |

*Primary Examiner*—Robert L. Griffin
*Assistant Examiner*—Joseph A. Orsino, Jr.
*Attorney, Agent, or Firm*—Toren, McGeady and Stanger

[57] ABSTRACT

A method and device for the automatic detection and evaluation of optical crack indication on the surface of workpieces is disclosed. In such method and device, visual displays are converted into electrical bright-dark signals by the use of light sensitive device, for example, an image recording tube. The surface under observation is scanned by the light-sensitive device line by line, the width of each of which (either as individual line or groups of adjacent lines) corresponds to the maximum optical display width from which evaluation is to proceed. The bright-dark signals thus obtained from three lines or lines groups are compared. From the signal of the middle line or line group and the signals of the two other line or line groups there is formed a difference signal which is evaluated to generate an error evaluation signal of a minimum value is exceeded.

26 Claims, 5 Drawing Figures

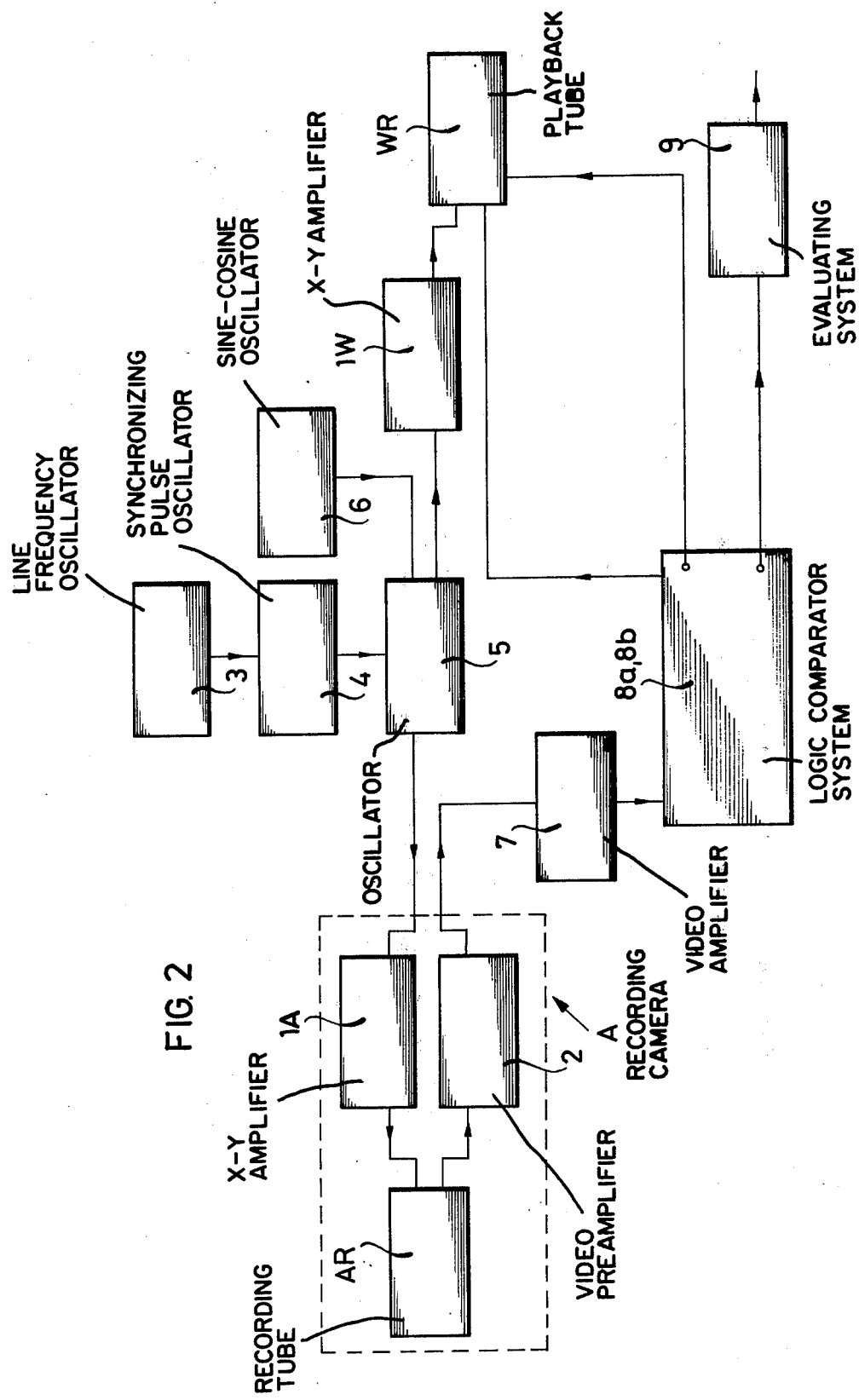

METHOD AND APPARATUS FOR THE AUTOMATIC RECOGNITION AND EVALUATION OF OPTICAL CRACK INDICATIONS ON THE SURFACE OF WORKPIECES

FIELD OF THE INVENTION

The invention relates to a method for the automatic detection and evaluation of optical crack indication on the surface of workpieces in which method the displays are converted into electrical bright-dark signals by the use of a light-sensitive device, for example, an image recording tube. The invention also relates to apparatus for performing this method.

The invention is to be used for the non-destructive testing of materials, namely for testing workpieces for the presence of surface cracks.

BACKGROUND OF THE INVENTION

Surface cracks are particularly dangerous faults in workpieces which are continuously stressed. Accordingly, components concerned with safety in the automobile industry must be non-destructively tested for freedom from cracks before they are installed. The magnetic powder method or the equally known dye penetration method is advantageously used to this end. In both methods the cracks, which cannot initially be recognized by the human eye, are displayed on the workpiece surface in a high-contrast and broadened form so that a tester can reliably recognize the indications.

Hitherto, such crack indications could be evaluated in practical industrial operation only by visual observation of the entire workpiece surface on the part of the tester. Such visual evaluation represents monotonous work, more particularly when testing mass-production components, and imposes a considerable stress on the eyes of the testing personnel. This has a detrimental effect on one's ability to concentrate. Moreover, subjective influences can hardly be excluded in visual evaluation. Reliable documentation of freedom from defects in industrial practice could therefore not be achieved in crack testing by means of the magnetic powder or dye penetration methods.

There is therefore an urgent need for facilities which are practicable in industrial terms to automate the operation of recognizing and evaluating the indications obtained in the non-destructive testing of workpieces for surface cracks.

According to the prior art, any departure from the magnetic powder method or the dye penetration method towards non-destructive materials testing methods which can be automated, for example ultrasonics, eddy current or stray flux measurements, is possible only if the specimens have a geometrical simple shape, testing can be confined to specific zones which are particularly endangered or if the defect direction can be predicted. Furthermore, the ability to recognize defects with this automatic method depends on surface texture so that by contrast to magnetic powder testing it is not possible to detect cracks whose depth does not substantially exceed the surface texture.

To detect hairline cracks in complicated workpieces with a cast or forged surface there are at present hardly any means other than the application of the magnetic powder method or the dye penetration method which necessitates visual evaluation of the indications thus obtained.

Efforts were made to achieve an improvement in the testing reliability by the use of indicating means which provide the greatest possible contrast of the crack indication on the workpiece surface, for example by black indicating means on a metallically bright surface, black or red means on a brightly dyed surface or by fluorescent indicating means which are brightly illuminated when observed in ultraviolet light, while the remaining surface remains dark.

Attempts have also been made to utilize such contrast, which increases optical recognizability, as the basis for automatic evaluation. For example, the illumination brightness of fluorescent indications was measured by means of photomultipliers. If the entire workpiece surface is covered in one pass, reliable recognition of crack indication is possible only if the remaining surface is kept free of fluorescent testing media. This procedure encounters difficulties in the case of rough surfaces; these retain a fine film of testing medium particles and, depending on the concentration of the testing medium fluid, results in a background brightness of greater or lesser intensity against which the additional brightness of a crack indication provides only a slight change.

As an alternative, there remained the restriction of the field of evaluation. Traversing over the workpiece surface made necessary thereby is time-consuming. It therefore also does not offer any solution to the problem because, dependent on the surface structure of the specimen or impurities in the testing medium fluid, it is possible for surface accumulations of testing medium to occur which in places can reach the brightness of the crack indication. These so-called apparent defects are however also evaluated by an observer. FIG. 1 shows a portion of a workpiece surface with a crack indication R and an apparent defect F.

It has already been proposed to utilize the different structure of crack indications and apparent defects and to use such difference as the basis for automating the evaluation of such indication. The different structure of the indication can be defined in terms of crack indications on the surface always having an elongated extent in one direction and being substantially narrower in the dimension at right angles thereto. To utilize this difference it was proposed to record the entire image and to store it electronically. The electronically stored image would then be tested by an electronic data processing plant to determine whether or not existing indications were line-shaped. The industrial use of this proposed method has not yet materialized due to the substantial effort required for storage and because of the very costly data processing plant.

It is the object of the present invention to provide means for automatically evaluating optical indications of cracks without such an effort but in addition to ensure that fault signals are delivered only by indications which are due to a surface crack and do not represent an apparent defect.

The method according to the invention is characterized in that the surface under observation is scanned by the light-sensitive device line by line, the width of each of which—either as individual line or as a group of adjacent lines—corresponds to the maximum optical display width from which evaluation is to proceed and that the bright-dark signals thus obtained from three lines or line groups, adjoining each other or separated from each other by an intermediate line and scanned in direct succession or simultaneously, where appropriate after storage of the signals associated with the first scanned two lines or line groups, are compared and from the signal of the middle line or line groups and the signal of the two other lines or line groups there is formed a difference which is evaluated to generate an error evaluation signal if a minimum value is exceeded.

Scanning of the observed surface can be performed in one operation by successive scanning of adjoining lines or groups of lines, where appropriate, accompanied by simultaneous scanning of every three adjoining lines or by the so-called line interlace method in which scanning is performed in two passes, offset by one line with respect to each other and by the omission of one line so that crack indications on the boundary between two lines or groups of lines can be evaluated with greater reliability. A three-gun image recording device, comprising three vidicons or a "chopped" vidicon can be used for scanning. With the present state of the art of image recording tube technology it appears to be more efficient to project the observed surface on the screen of a single-gun image recording apparatus and to successively scan the three lines or groups of lines on which evaluation is based by means of one electron beam and by storing the bright-dark signals of the two first-scanned lines or groups of lines. The surface to be tested can also be scanned through line by line illumination with one or more light beams or laser beams.

To evaluate indications of any random direction the surface image can be mechanically, optically or electronically rotated during one testing cycle.

To specify a minimum length of optical indication as the limit for the commencement of evaluation, it is possible to arrange for the bright signals to be evaluated only onwards from a specified minimum appearance time.

Surface regions with defect indications can be blocked out mechanically, optically or electronically.

SUMMARY OF THE INVENTION

Apparatus for performing the method according to the invention is characterized by a control system for the light-sensitive device which scans the surface under observation in lines, the width of which, either as individual line or as a group of adjacent lines, corresponds to the maximum optical display width from which evaluation is to proceed, and by a logic comparator circuit for the bright-dark signals thus obtained from three lines or line groups adjoining each other or separated from each other by an intermediate line and directly successively or simultaneously scanned, to deliver an error evaluation signal only if the difference between the signal of the middle line or line group and the signals of the two other lines or line group exceeds a minimum value. The control system can effect scanning by the so-called line interlace method in which scanning is performed by the omission of one line at a time.

One advantageous embodiment of apparatus of this kind is characterized in that the light-sensitive device comprises a recording camera for the projection of the observed surface on the screen of a recording tube whose electron beam, which scans the said screen line by line, is controlled by a line frequency oscillator which defines the line traversing rhythm, by a synchronizing pulse oscillator, connected downstream thereof and effecting flyback dark control and by a horizontal and by a vertical oscillator and whose video signals are amplified and are supplied to the logic memory and comparator system.

Advantageously, such apparatus also embodies a playback tube which is driven by the control system for the recording tube and reproduces the image of the observed surface and whose control grid is connected to the output of the logic comparator system.

The surface image is rotated optically, for example through mirror systems, or electronically, for example by modulation of the deflection voltages for the scanning beam or the scanning beams are rotated by means of a sine-cosine oscillator so that it is possible to evaluate indications in any direction and not only those whose direction happens to be orientated in the line direction. Mechanical relative rotation between object and scanning device can also be used to this end.

Three-gun tubes can be used in place of single-gun recording and playback tubes or it is possible to use tubes which simultaneously scan over three lines by means of "chopping", storage of the bright-dark signals being omitted.

The light-sensitive device for scanning the observed surface can also comprise apparatus for light beam or laser beam scanning.

Further features and advantages of apparatus according to the invention are disclosed in the description hereinbelow of one exemplified embodiment of such apparatus and three exemplified circuits for such apparatus as illustrated in the accompanying drawings.

BRIEF DESCRIPTION OF THE DRAWINGS

FIG. 2 is a block circuit diagram of an exemplified embodiment of apparatus according to the invention and FIGS. 2a to 2c show different embodiments of a logic memory and comparator circuit of the apparatus according to FIG. 2 in the form of a block circuit diagram.

DESCRIPTION OF THE PREFERRED EMBODIMENTS

Figure 1:
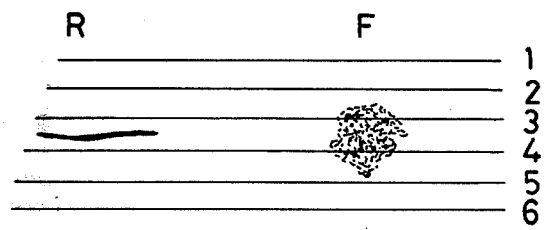
FIG. 1 is a section of an observed surface, indicating the scanning lines and showing a crack indication R and an apparent defect F.

The apparatus illustrated in FIG. 2 is provided with a recording camera A in the form of a single-gun image recording unit for scanning the observed surface. The camera A contains a recording tube AR, an x-y amplifier 1A for deflecting the electron beam which scans the observed surface image projected on the screen of the tube AR line by line, and a video preamplifier 2 for preamplification of the bright-dark signals scanned by the electron beam.

The apparatus is also provided with a playback tube WR preceded by an x-y amplifier 1W.

The rhythm at which the electron beams traverse the screens of the recording tube as well as of the playback tube is defined by a line frequency oscillator 3. A synchronizing pulse oscillator 4, connected downstream thereof, ensures that the electron beams act in only one direction over the screen, i.e. they are driven into the dark signal on flyback. The deflection voltages for the electron beam of the recording tube AR and of the playback tube WR are produced by a horizontal and vertical oscillator 5. These deflection voltages which define the deflection of the electron beams in the x and y direction, are modulated by a sine-cosine oscillator 6 in the sense that a cosine oscillation is superimposed on the y deflection frequency if a sine oscillation is simultaneously superimposed on the x deflection frequency. The polarity of one of the two deflection directions of the playback tube WR must be reversed with respect to the recording tube AR.

The image produced by line scanning of the recording tube will then rotate at a rhythm which corresponds to the frequency of the sine-cosine oscillator 6, for example in the clockwise direction. The different polarity of a deflection device for the playback tube WR ensures that in this case the playback image rotates anticlockwise with respect to the recorded image and thus again appears as a stationary image.

The bright-dark signals scanned by the recording tube AR are amplified by video amplifiers 7. The video signal is evaluated in downstream-connected memories and a logic comparator system.

Figure 2C:
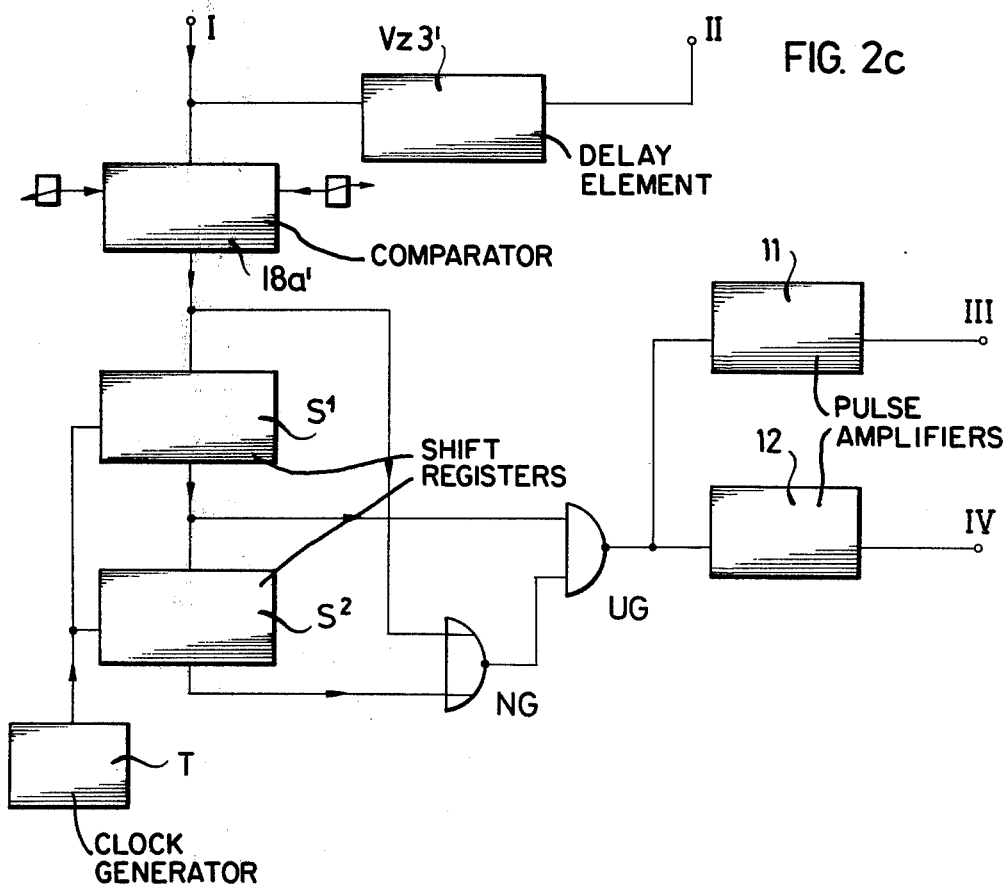
Figure 2A:
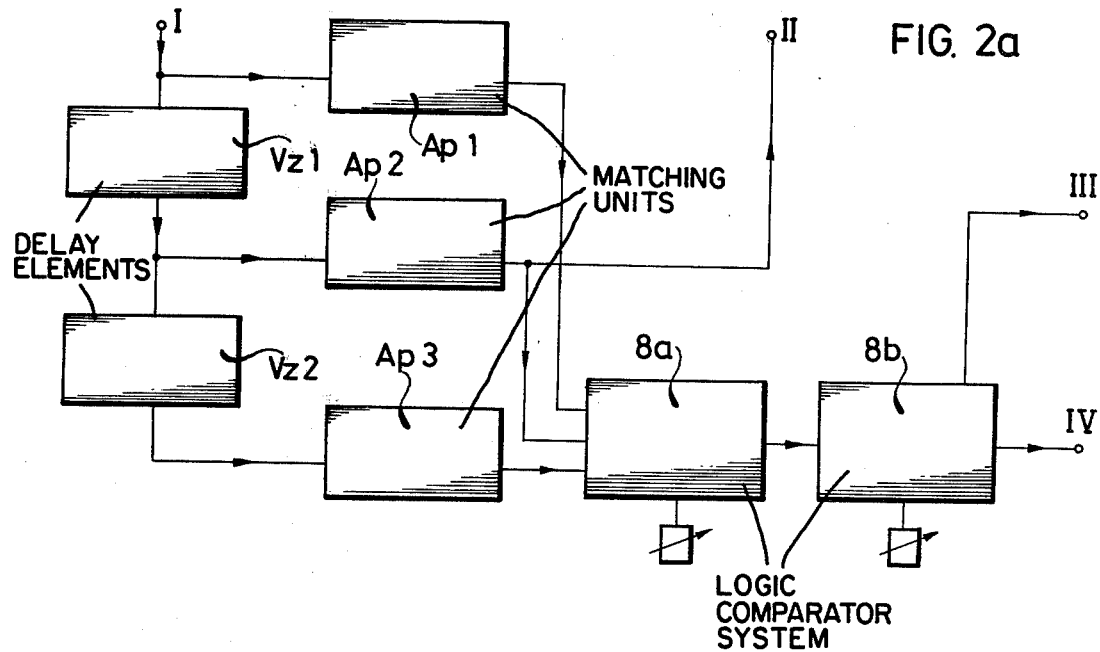

FIG. 2a shows the block circuit diagram of a circuit for analog processing of the video signal in a logic comparator system $8a$, $8b$ preceded by memory elements. Specifically, block $8a$ of the logic comparator system comprises the comparator $8a$ and the logic system $8b$. These comprise three parallel-connected signal matching units Ap1, Ap2 and Ap3, connected between the input I for the video signal of the camera A and the comparator $8a$, a delay element Vz1 preceding the signal matching unit Ap2 and having a delay corresponding to the line transit time and a delay element Vz2, additionally preceding the signal matching unit Ap3 and having the same delay time as Vz1. The video signal is delivered at the signal output of the matching unit Ap2 with a delay corresponding to the transit time of one line and is delivered at the output of the signal matching unit Ap3 by a delay corrresponding to the transit time of two lines. Accordingly, three different signals are simultaneously available, namely the direct bright-dark signal at the output of the signal matching unit Ap1, the bright-dark signal of the preceding line at the signal output of the matching unit Ap2 and the bright-dark signal of the penultimate line at the output of the signal matching unit Ap3.

The signal at the signal output II of the matching unit Ap2 is utilized for bright-dark control of the playback tube WR and accordingly produces an image of the entire surface portion covered by the recording tube WR. The signals of the middle of the three lines which are to be simultaneously evaluated appear at the output of the signal matching unit Ap2 and are supplied directly to the comparator $8a$ in the same way as the signals appearing at the outputs of the signal matching units Ap1 and Ap3, i.e. the signals of the two outer lines.

The comparator $8a$ which is adjustable in terms of its preset "brightness" value delivers a signal only if a signal appears in the signal matching unit Ap2 but not in the signal matching units Ap1 and Ap3.

The control grid of the playback tube WR is connected to the output III of a logic system $8b$ connected downstream of the comparator $8a$. The image therefore appears in particularly bright form at the place at which an output voltage occurs in the comparator $8a$. This place in the image is identical with the place which is to be interpreted as a line-shaped indication. The playback tube will therefore display an image of the entire surface region covered by the recording tube, on which said surface region the indication that is to be evaluated is illuminated at the frequency of the sine-cosine oscillator.

Figure 2B:
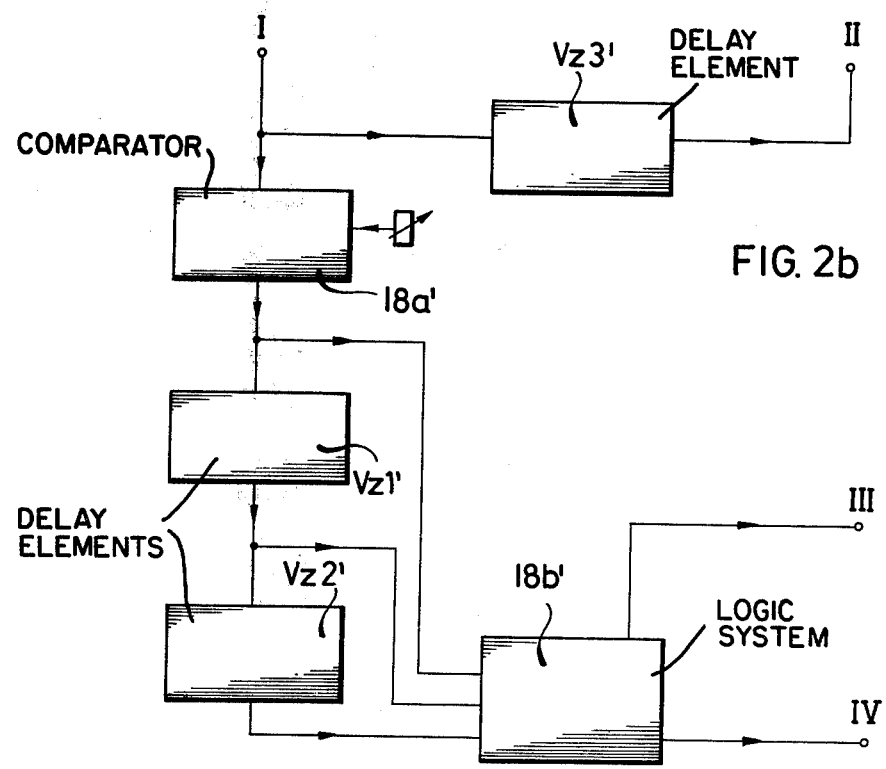

In addition to the facility of analog storage (or delay) of the video signal there is also the facility of comparing the video signal directly downstream of the video amplifier 7 with a set point associated with brightness and with a set point associated with crack length. A circuit suitable to this end is illustrated in FIG. 2b. The video signals supplied to the input I of this logic memory and comparator circuit are supplied to a comparator $18a'$ which is adjustable in terms of the "brightness" and "crack length" set points. Digital data delivered by the comparator output is delayed by the transit time of one line through two delay elements $Vz1'$ and $Vz2'$ connected in series between the comparator output and a logic system $18b'$. Data appearing at the comparator output, at the output of the delay element $Vz1'$ and at the output of the delay element $Vz2'$ are supplied to the logic circuit $18b'$. This delivers a signal only if the output of the delay element $Vz1'$ delivers data but no data is delivered by the output of the comparator $18a'$ and of the delay element $Vz2'$.

The output III of the logic circuit $18a'$ is utilized for brightness control of the playback tube WR. To obtain line synchronism between the bright keying pulse and the video signal the latter is applied via a delay element $Vz3'$ to the playback tube WR.

FIG. 2c shows one possible modification of the circuit according to FIG. 2b. The function of the delay elements $Vz1'$ and $Vz2'$ of the circuit according to FIG. 2b is performed in this case by shift registers S1 and S2 operating in conjunction with a clock generator T. The logic circuit comprises a NOR-network NG and an AND-network UG as well as pulse amplifiers 11 and 12. The output III of the pulse amplifier 11 is connected to the control grid of the playback tube WR and the output IV of the pulse amplifier 12 in the same way as the outputs IV of the logic circuit according to FIGS. 2, 2a and 2b can be connected to an evaluating system 9 so that the signal from this output can be utilized for automatic defect evaluation. The image on the playback tube is of no significance for such evaluation. However, it is useful for setting up or for optimum adjustment of the device with respect to the object under test.

A tube, having three simultaneously scanning beams, can also be used for recording. This enables the following circuit to be simplified. The three simultaneously appearing signals from three adjacent lines can then be connected directly to signal matching circuits Ap1, Ap2 and Ap3 thus eliminating the expenditure required for the memory system.

The object can also be directly scanned with a light beam or laser beam instead of projecting the observed object on the screen of a recording tube and for the image thus produced to be scanned in lines.

Apart from presetting the line width as a limit for recognizing an indication as being line-shaped this can also be achieved by three identical groups of adjoining lines being compared with each other instead of three individual adjoining lines in terms of the scanning results.

After comparing the results from three lines or groups of lines the result of the third line or groups of lines is stored, the fourth line or groups of lines is scanned and comparison of the result of the third line or groups of lines with the results of the second and fourth line or groups of lines is again triggered and so on.

As regards the definition of a line it is important that the length of the indication is greater than its width. Values of a length-width ratio below which the indication is not to be regarded as a line is a question of definition. The minimum length which an indication must have in order to be evaluated can be adjusted by pre-defining a minimum time during which a bright signal must appear. The width of the lines or groups of lines can be selected so that a maximum width of indication is preprogrammed.

Rotation of the object image through at least 180° or better through 360° can be obtained mechanically by relative rotation of the object and scanning device or optically by rotation of the object image by the provision of mirrors in addition to the electronic method explained by reference to FIG. 2.

In practice it frequently occurs that the surface to be tested has line-like indications of which it is known that they are not cracks (for example sharp edges, punched numbers or letters, edge contours and the like). The defects which would thus be indicated can be avoided by blocking-out measures or devices. A strip, attached to the screen of the recording tube at the place at which the defect indication would appear is a mechanical blocking-out device. Optical blocking-out can be performed for example by fading a light strip into the image on the recording screen, such light strip exceeding the minimum width defined for recognizing the indication so that the said light strip is not evaluated.

Finally, electronic blocking-out, in which the electron beam is keyed out in the region and in the direction of the defect indication, is also feasible.

In the above-described embodiment scanning is performed progressively line by line, three directly adjacent lines or groups of lines forming an evaluation unit on which signal comparison is performed. By contrast thereto it is also possible to operate by the so-called line interlace method. In this method, also referred to as "half-image method", every second line is omitted in scanning. During the first scanning pass only every second line of the observed surface is scanned and in a second, succeeding scanning pass the lines omitted during the first scanning pass are then scanned. This method offers a greater degree of reliability of evaluating line-shaped indications even in cases in which a narrow optical crack indication is situated at the limit between two lines or groups of lines and scanning without line interlace in two adjacent lines or groups of lines would cover one evaluation unit which would erroneously not be interpreted as a line. The line interlace ensures that each signal of a crack indication is covered at least once at an adequate distance from adjacent lines or groups of lines.

We claim:

1. A method for the detection of cracks on the surface of workpieces, in which method, the surface is scanned line by line and image signals are generated, comprising the steps of:
   (a) scanning the surface of a workpiece line by line employing individual scanning lines each having a width corresponding to the N-th part of the maximum crack width, from which evaluation is to proceed, N being an integer number;
   (b) comparing the image signals of N successive scanning lines with the image signals of N preceding and of N succeeding successive scanning lines; and
   (c) generating a defect evaluation signal if the difference between the image signals of the N scanning lines and the image signals of the N preceding and the N succeeding scanning lines exceeds a predetermined minimum value.

2. The method according to claim 1, wherein said generating step generates a defect evaluation signal only if the predetermined minimum value is exceeded at least for a predetermined minimum time.

3. The method according to claim 1, including the step of rotating the direction of the scanning lines relative to the surface of the workpiece.

4. The method according to claim 1, wherein the scanning step is performed in two passes and that with each of these passes N lines are omitted after each scanning of N lines and in the second pass the lines omitted in the first pass are scanned.

5. The method according to claim 1, wherein $N > 1$.

6. The method according to claim 5, wherein three times N lines are scanned simultaneously.

7. The method according to claim 5, wherein N lines are scanned in succession with storage of the image signals of any firstly scanned N lines and of any secondly scanned lines.

8. The method according to claim 1, including omitting the given features of the surface of the workpiece which have a structure similar to cracks and which would generate a defect signal when scanning the surface or evaluating the image signals.

9. Apparatus for the detection of cracks in a workpiece comprising:
   an electro-optical device for line-scanning the surface of the workpiece and for generating image signals of the individual scanning lines;
   a control device for regulating the width of each scanning line so that it corresponds to the N-th part of the maximum crack width from which evaluation is to proceed, N being an integral number;
   a comparator circuit for comparing the image signals of the scanning lines including a logic circuit for comparing the image signals of N successive scanning lines with the image signals of N preceding and N succeeding successive scanning lines; and
   a system for generating a defect indicating signal if the difference between the image signals of the N scanning lines and the image signals of the N preceding and the N succeeding successive scanning lines exceeds a pre-defined minimum value.

10. Apparatus according to claim 9, wherein said logic circuit generates a defect indicating signal only if the pre-defined minimum value is exceeded for at least a pre-defined minimum time.

11. Apparatus according to claim 9, wherein the electro-optical device includes a recording camera, a recording tube having a screen, frequency oscillator, synchronizing pulse oscillator and horizontal and vertical oscillator, said camera for the projection of an image the observed surface by optical means on the screen of said recording tube, said recording tube having an electron beam which scans the said screen line by line, and wherein said tube is controlled by a control system including said frequency oscillator for defining a line traversing rhythm, said synchronizing pulse oscillator responsive to said frequency oscillator and effecting flyback dark control and a horizontal and vertical oscillator and wherein video signals developed by said recording tube are amplified by amplifying means and are then supplied to the comparator circuit.

12. Apparatus according to claim 11, wherein deflection voltages control movement of said beam including a sine-cosine oscillator for modulating deflection voltages for the scanning beam.

13. Apparatus according to claim 11, including a playback tube which is driven by the control system for the recording tube and reproduces the image of the observed surface and whose control grid is connected to the output of the comparator circuit.

14. Apparatus according to claim 9, wherein the electro-optical device includes a three-gun recording tube whose electron beams simultaneously scan three adjacent lines and that the video signals thus obtained are amplified by an amplifier which is connected with the comparator circuit.

15. Apparatus according to claim 9, wherein an optical device is included for the continuous rotation of the image or of the object under test or of the scanning device through an angle of at least 180°.

16. Apparatus according to claim 15, wherein said angle is preferably 360°.

17. Apparatus according to claim 9, wherein the electro-optical device includes a device which illuminates the observed surface line by line with one or more light beams or laser beams.

18. Apparatus according to claim 9, including memory circuits for the image signals of each pair of N scanning lines scanned firstly and secondly.

19. Apparatus according to claim 17, wherein the memory circuits includes three parallel-connected signal matching devices (Ap 1, Ap 2, Ap 3) connected between a video amplifier output and a comparator and including a delay element preceding the signal matching device (Ap 2) and having a delay corresponding to the line transit time and a delay element additionally preceding the signal matching device (Ap 3) and having the same delay time, the output signal being utilized by the signal matching device (Ap 2) for bright-dark modulation of a playback tube.

20. Apparatus according to claim 18, wherein the delay elements which follow the comparator are formed by shift registers in association with a clock generator and said comparator circuit includes a NOR-network, an AND-network and two pulse amplifiers.

21. Apparatus according to claim 9, including a device for blocking out surface regions with fault indications which are not cracks.

22. Apparatus according to claim 9, including a control system for the electro-optical device and adapted to effect scanning by jumping one line at a time (line interlace method).

23. Apparatus according to claim 9, wherein a mechanical device is included for the continuous rotation of the image or of the object under tests or of the scanning device through an angle of at least 180°.

24. A method for the detection of cracks on the surface of workpieces, in which method, the surface is scanned line by line and image signals are generated, comprising the steps of:
(a) scanning the surface of a workpiece line by line employing individual scanning lines each having a width corresponding to the maximum crack width from which evaluation is to proceed;
(b) comparing the image signal of a given scanning line with image signal of a preceding and a succeeding scanning line; and
(c) generating a defect evaluation signal if the difference between the image signals of the given scanning line and the image signals of the preceding and succeeding scanning line exceeds a predetermined value.

25. The method according to claim 24, wherein three lines are scanned simultaneously.

26. The method according to claim 24, wherein the individual lines are scanned in direct succession with the storge of the image signals of each pair of firstly and secondly scanned lines.

* * * * *